United States Patent [19]

Wallace et al.

[11] Patent Number: 4,789,663

[45] Date of Patent: Dec. 6, 1988

[54] METHODS OF BONE REPAIR USING COLLAGEN

[75] Inventors: Donald G. Wallace, Menlo Park; Thomas L. Smestad, Palo Alto; John M. McPherson, Sunnyvale; Karl A. Piez, Menlo Park; Saeid Seyedin, Sunnyvale; Rosa Armstrong, Palo Alto, all of Calif.

[73] Assignee: Collagen Corporation, Palo Alto, Calif.

[21] Appl. No.: 752,447

[22] Filed: Jul. 5, 1985

Related U.S. Application Data

[63] Continuation-in-part of Ser. No. 628,335, Jul. 6, 1984, abandoned, Ser. No. 628,404, Jul. 6, 1984, abandoned, Ser. No. 628,328, Jul. 6, 1984, abandoned, and Ser. No. 628,409, Jul. 6, 1984, abandoned.

[51] Int. Cl.$^4$ ............... A61K 37/12; A61K 35/32; C07K 15/20; C12P 21/00

[52] U.S. Cl. .................................. 514/21; 514/2; 514/801; 424/95; 424/423; 424/443; 530/356; 435/68; 128/92 W

[58] Field of Search ............. 424/95, 443, 423; 514/2, 21, 801; 530/356; 128/92 C, 92 G; 435/68

[56] References Cited

U.S. PATENT DOCUMENTS

| | | | |
|---|---|---|---|
| 2,621,145 | 12/1952 | Sano | 167/84 |
| 3,318,774 | 5/1967 | Dingwall | 167/74 |
| 3,443,261 | 5/1969 | Battista | 3/1 |
| 3,458,397 | 7/1969 | Myers et al. | 424/95 |
| 3,820,167 | 6/1974 | Sivash | 3/1 |
| 3,918,100 | 11/1975 | Shaw | 3/1.9 |
| 3,919,723 | 11/1975 | Heimke | 3/1.9 |
| 3,949,073 | 4/1976 | Daniels | 514/801 |
| 4,066,083 | 6/1978 | Ries | 128/325 |
| 4,140,537 | 2/1979 | Luck | 106/155 |
| 4,186,486 | 2/1980 | Gordon | 433/201 |
| 4,294,241 | 10/1981 | Miyata | 128/156 |
| 4,294,753 | 10/1981 | Urist | 260/112 R |
| 4,314,380 | 2/1982 | Miyata | 3/1.9 |
| 4,394,370 | 7/1983 | Jefferies | 424/15 |
| 4,434,094 | 2/1964 | Seyedia | 260/112 R |
| 4,440,750 | 4/1984 | Glowacki | 424/95 |

FOREIGN PATENT DOCUMENTS

| | | |
|---|---|---|
| 0012443 | 12/1979 | European Pat. Off. . |
| 0012959 | 12/1979 | European Pat. Off. . |
| 0071242 | 7/1982 | European Pat. Off. . |

OTHER PUBLICATIONS

Cucin, R. L. et al., *NY State Jour. Med.*, 11/1979, 1856–1857, "Experimental Bony Defects".

Hayashi, K., *Arch Orhop Traumat Surg* (1982) 99: 265–269, "Repair of Experimental Bone Defect with a Collagen Block Containing Synthesized Apatite".

Jaffee, A. et al., *Archs Oral Biol*, (1978) 12:415–419, "Biological Anchoring of Acrylic Tooth Implants in the Dog Using Enriched Collagen Solutions".

Krekeler, G. et al., *Int J. Oral Surg.* (1981) 10: Suppll 151–155, "The Healing of Autologous Spongiosa and Heterologous Materials in the Periodontal Bone Pocket".

Joos, U. et al., *Biomaterials,* (1980) 1:23–26, "Influence of Collagenfleece on Bone Regeneration".

Jaffe, A. *Archs Oral Biol,* (1982), 27:99–1001, "One-Year Follow Up for the Use of Collagen for Biological Anchoring of Acrylic Dental Roots in the Dog".

*Primary Examiner*—J. R. Brown
*Assistant Examiner*—Jacqueline M. Stone
*Attorney, Agent, or Firm*—Ciotti & Murashige, Irell & Manella

[57] ABSTRACT

A method of repairing bone defects by use of suspensions containing purified atelopeptide, reconstituted, fibrillar skin collagen or bone collagen powder or mixtures thereof is disclosed. The suspensions provide matrices for conductive growth of bone into the defect. The skin collagen may also be lyophilized and used in the form of mats.

10 Claims, No Drawings

METHODS OF BONE REPAIR USING COLLAGEN

CROSS-REFERENCE TO RELATED APPLICATIONS

This is a continuation-in-part of U.S. Ser. Nos. 628,335, 628,404, 628,328 and 628,409 all filed July 6, 1984 and now abandoned.

TECHNICAL FIELD

This invention relates to the field of bone repair in vertebrates, especially mammals and humans. More specifically, the invention relates to a method of repairing bone which utilizes a collagen-based implant material to facilitate repair by bone conduction. This collagen material is highly purified and non-immunogenic, and may, if desired, be xenogeneic. The collagen is a reconstituted material from skin or a bone derived material or mixture thereof.

BACKGROUND ART

The problem of effecting repair of defective bones has plagued mankind for centuries. Until relatively recently, the only practical course was to immobilize broken bones and to rely on nature to effect regrowth of skeletal tissue into an injury. Only with the advent of the possibility of surgery has it been possible to utilize implanted bone substitutes, not only to replace injured or diseased bone structures, but also to repair congenital or degenerative defects in the skeletal structure.

A wide range of materials have since been utilized, and elaborate designs have been disclosed for replacements of entire portions of bones, for example hip joints (U.S. Pat. No. 3,820,167) and teeth (U.S. Pat. No. 4,186,486). Materials employed have included metals such as titanium (EPO Publication No. 0071242, published Feb. 9, 1983; U.S. Pat. No. 3,918,100), ceramics such as aluminum oxide (U.S. Pat. No. 3,919,723), shaped and treated bone (U.S. Pat. No. 3,318,774), and various bone preparations such as, for example, bone dust compacted into flexible mats (U.S. Pat. No. 2,621,145).

It has long been understood that skeletal structures have inorganic and organic components. The mineral component which, presumably, accounts for the strength and rigidity of bone structure is predominantly a form of calcium phosphate, hydroxyapatite. The organic component is chiefly composed of a single type of protein, collagen, which serves to impart a measure of resilience thus preventing the structures from being unduly brittle. As skeletal tissue is alive, of course, additional metabolically active organic components must be included in the structure, and it is these bone cells and their active metabolites which are responsible for the naturally occurring healing and maintenance processes.

However, since the major components of bone from a quantitative standpoint are collagen and ceramic, various reconstituted implant preparations involving mixtures of similar or different ceramic materials and various types of collagen preparations have also been employed. For example, see U.S. Pat. No. 3,443,261, Hayashi, K., et al, *Arc Orthop Traumat Surg* (1982) 99: 265; and U.S. Pat. No. 4,314,380).

It has been determined that bone tissue repair occurs by one of two alternative mechanisms, or a combination of both. In conductive repair, cells which are already committed to their character as bone cells (osteoprogenitor cells) move into the space of the defect from adjacent bone, and form bone directly. No special factors (other than non-specific nutrients) are required. In induction, however, this process is preceded by conversion of previously uncommitted multipotential cells into osteoprogenitor cells which first form cartilage that calcifies and degenerates and is replaced by bone. In order to acquire the capacity to do this, specific protein factors are required. The nature of these factors is not at present understood. For either conductive or inductive repair, it is required that the living tissue of the host provides the ultimate skeletal structure. Thus the implant which mediates these processes serves not as a substitute for the defective or removed bone, but rather as a matrix support for active replacement of the missing tissue.

Accordingly, attempts have been made to devise implants for defective skeletal tissue or lesions in bones and teeth which are intended precisely for this purpose. These implants do not attempt to mimic the composition of the missing bone, but rather to serve as a structural support and a guiding matrix for encroaching bone deposits derived ultimately from the adjacent fresh bone. These supports may provide only matrix support functions, i.e., mediate conductive repair, or may, in addition, include factors which stimulate the differentiation of uncommitted cells to osteoprogenitor cells by providing what are currently known as "osteogenesis factors" (OF) or "bone morphogenic proteins" (BMP). Because collagen is already a familiar material to the metabolically viable cells associated with bone growth, attempts have been made to use implants which are composed predominantly of collagen for both inductive and conductive bone repair.

For implants useful in inductive repair, U.S. Pat. No. 4,294,753 discloses a process for preparing a bone morphogenic protein. A purification procedure for an OF which is probably not identical to the BMP of the foregoing patent is disclosed in U.S. Pat. No. 4,434,094 issued Feb. 28, 1984. These factors reside naturally in bone, and preparations of demineralized bone particles, which are used in construction of implants, presumably release this factor in operable form. Both purified and unpurified forms of these factors have been used in various implants.

Other workers have disclosed the results of attempts to utilize collagen preparations alone as a matrix for conductive bone repair activities, i.e., preparations which do not contain factors for maturation of progenitor cells into osteogenic cells, and thus mediate conductive repair.

Krekeler, V. G., et al, *J Oral Surg* (1981) 10: Suppl. 1: 151 compared the utility of autologous spongiosa, a preparation of collagen (Collagenfleece ®, Pentapharm) and binding gelatin as fillings for peridontal defects in beagles. The preparations were simply packed into the bony cavities artificially created, and the healing processes followed by polychrome sequential labeling. Collagenfleece ® was found to mediate the healing, but was less effective than the autologous spongiosa transplants.

The Collagenfleece ® used in the preceding preparation is derived according to a procedure disclosed in U.S. Pat. No. 4,066,083 from pigskin. The skin is finely divided, degreased using detergent, washed, and digested with pepsin to give a viscous suspension, and the collagen precipitated by addition of saturated salt solution. The precipitate is suspended in acid, reprecipitated as a fibrous white precipitate in salt solution, washed as many times as desired, and desalted by washing with alcohol. The purified collagen is suspended in acid solution and freeze dried. It is sterilized by γ-irradiation, which may degrade or cross link the preparation. This preparation is available commercially under the name Collagenfleece ® and has been used in a number of other bone repair studies.

Joos, U., et al, *Biomaterials* (1980) 1: 23-26, utilized Collagenfleece ® as an implant in artificially damaged rabbit mandibles and found that after 2 weeks, the defects were filled with cancellous bone particles and showed complete ossification after 4 weeks. Zetzmann, D., et al, *Schweiz Mschr Sabnhelik* (1982) 92: 119 also achieved bone regeneration in facial surgery upon use of Collagenfleece ® as an implant. Springorum, H. W., et al, *Z Orthop* (1977) 115: 686 obtained similar results using Collagenfleece ® in a cortical layer defect.

Jaffee, A., et al, *Archs Oral Biol* (1978) 23: 415; ibid. (1982) 27: 999 reported successful anchoring of acrylic tooth implants in dogs using collagen solutions which were prepared from dog skin by extraction with acetic acid and trichloroacetic acid/ethanol purification. The successful anchoring of the implants was intact after a year.

Cucin, R. L., et al, *New York State Journal of Medicine* (1979) 1856 used atelopeptide collagen from calf skin, which had been gamma irradiated, for rib repair in rabbits and, when supported by gelatin sponge material or with autologous bone dust, to repair skull holes in dogs.

A preparation of collagen, presumably still containing the teleopeptides, and cross-linked by gamma irradiation was employed in filling tooth pulp cavities and as an under the skin "bone replacement" implant as disclosed in, respectively, EPO Publication No. 0012443 published June 25, 1980 and EPO publication No. 0012959, published July 9, 1980.

None of the foregoing collagen repair procedures are completely successful. Either inflammation occurs, particularly where xenogeneic collagen is used, or healing is unsatisfactory. The present invention provides an implantable collagen preparation which is capable of conducting the ingrowing bone repair tissue from dedicated bone cells into the defect whose repair is desired. Because xenogeneic collagen can be used, large amounts are obtainable and the method can be widely applied. In addition, the invention provides bone repair compositions which offer great versatility in being adaptable to a wide range of stress-bearing requirements.

DISCLOSURE OF THE INVENTION

The present invention provides a method of repairing bone defects or reconstructing the skeletal matrix of a mammal, in particular a human, by implanting in the defect purified, non-immunogenic collagen which is derived, if desired, from a species other than that being repaired. Thus, the invention provides a method for mediating the subject organism's natural mechanisms for bone defect repair by using a collagen preparation of general applicability which is highly purified, and which is successful in providing a matrix for new bone growth.

In the method of the invention, fresh bone containing living osteoprogenitor cells is exposed to a bone defect and placed into contact with a preparation of collagen which is a composition derived from either or both of two sources, bone and skin. The bone derived collagen is prepared from demineralized bone (DMB), and consists essentially of Type I collagen having the telopeptides effectively removed. It is obtained by treating DMB with a non-collagenase protease, such as trypsin, which both destroys factors mediating inductive repair and removes the telopeptides. The resultant material is obtained in powder form and can be designated bone collagen powder (BCP). The skin derived collagen is chiefly Type I collagen which includes a small amount of Type III and is typically obtained from calf skin. This type of collagen is commercially available under the trademark Zyderm ® collagen implant (ZCI). The collagen preparation typified by ZCI is a reconstituted fibrillar form of atelopeptide collagen. In addition, the skin derived collagen preparation can be lyophilized before being used in the implant.

By varying the ratio of BCP to ZCI in a mixture of these peptides, the physical properties of the repair material can be adjusted to conform to the particular demands of the environment of the defect.

Thus in one aspect, the invention relates to a method of repairing bone defects which method comprises
 (a) exposing fresh bone surface bearing living osteoprogenitor cells to the defect;
 (b) placing into the defect and into contact with fresh bone surface a preparation of collagen. The collagen preparation is either purified reconstituted atelopeptide fibrillar skin collagen or bone collagen powder (as defined below) or a mixture thereof.

The purified reconstituted fibrillar collagen may be in lyophilized form. This lyophilized preparation (lyophilized collagen gel or LCG) has favorable handling properties and can be formed by rolling or casting the original gel preparation into sheets which are then lyophilized and can be easily manipulated into implants.

The skin derived collagen is typically obtained from skin in a process wherein it has been dissociated into solubilized form, sterilized by filtration, and then reconstituted into fibrillar form after removal of the telopeptides. A typical preparation has been described as useful for soft tissue repair, and is commercially available for that purpose under the trademark Zyderm ® collagen implant (ZCI). Methods to prepare it are extensively described in U.S. Pat. No. 3,949,073.

The bone collagen powder is derived from demineralized bone (DMB) and consists essentially of Type I collagen having the telopeptides removed. It is obtained by treating DMB with trypsin, which destroys both factors responsible for osteogenesis and the telopeptides. The resulting bone collagen powder (BCP) has the above-mentioned desired properties, as well as the capability to withstand stress and to provide weight-bearing support for the skeletal defect.

In other aspects, the invention relates to the collagen preparations useful in this invention and to their methods of preparation.

MODES OF CARRYING OUT THE INVENTION

A. Definitions

As used herein, "conductive" repair of bone defects refers to a process for replacing lost bone or for growing desired new bone, which involves the metabolism of previously committed osteoprogenitor cells. These cells are capable of producing cartilage and/or bone without induction by protein factors generally known as osteogenic or morphogenic. The process includes mechanisms whereby osteogenesis is directly effected by the committed cells, but not those wherein there is a requirement for externally and deliberately added protein factors to produce committed cells.

It is realized that conversion of undifferentiated cells to osteoprogenitor cells may still be effected by indigenous proteins. However, as herein defined, "conductive" bone repair is mediated by external supply only of supporting matrix, and does not provide an external source of living tissue or of non-indigenous osteogenesis factor.

"Bone defect" refers to a space in the skeletal system in which it is desired that bony tissue be deposited, whether the space is created by injury to the subject, or by a malformation or degeneration of the subject's skeletal system. Such defects may be the result of simple bone breakage, decay of bone tissue because of disease, surgical removal of diseased bone tissue or of unwanted malformations, or of reconstructive or cosmetic surgery.

"Fresh bone" refers to bone in the skeletal system of the subject organism which is in healthy condition and which is treated, such as by cutting, to expose living tissue. It is found that in the method of the invention, contact is required of fresh bone with the collagen implant which provides a matrix in the defect area in order to provide the viable cells for regeneration of bone within the defect and to utilize the collagen matrix provided.

"Preparation of collagen" refers to a composition which contains as its major component some form of collagen protein.

"Xenogeneic" refers to a species which is different from that of the subject being treated.

"Free from impurities" or "purified" refers to those impurities which are normally associated with the collagen or other preparation in its natural state. Thus, collagen prepared from calf skin is free from impurities when substantially all other components of calf skin have been substantially removed; that from bone, when substantially all other components of bone are eliminated.

"Reconstituted" collagen refers to collagen which has been disassembled into individual triple helical molecules with or without their telopeptide extensions and brought into solution, and then regrouped into "fibrillar" form. In this form, the fibrils consist of long, thin collagen molecules staggered relative to one another by multiples of about ¼ of their length. This results in a banded structure which can be further aggregated into fibers.

"Substantially free of cross-linking" refers to collagen which has undergone removal of the telopeptides, so as to result in a preparation lacking the native capacity for cross-link formation. Since the reactive groups responsible for native cross-linking reside in these telopeptide portions, there is substantially no capacity to cross-link using the indigenous chemistry remaining. Such preparations, therefore, remain substantially cross-link free if not deliberately cross-linked using reagents which generate cross-links using other mechanisms such as by treating with glutaraldehyde, or subjecting the molecules to treatment imposing a spurious form of such linkage. For example, treatments often used for sterilizing purposes, such as high temperature and γ-irradiation have the effect of causing the formation of additional cross-links between helices. In the preparation used in the invention, the skin-derived collagen is sterilized by microfiltration while still in solution and handled under sterile conditions thereafter, thus avoiding the result of unwanted cross-link formation.

"Bone collagen powder" (BCP) refers to a purified atelopeptide preparation of collagen derived from demineralized bone. This preparation consists essentially of collagen per se, and does not contain metabolically active proteins. As it originates in bone, it is composed of Type I collagen, and its molecular architecture mimics the native 3-dimensional structure found in bone.

B. Detailed Description

B.1 Applications

The bone defects to which the invention applies include any cavity in osseous tissue whose filling is required in order to integrate the skeletal system. Medical or veterinary procedures of bone defect repair which are appropriate as vehicles for the use of the method of the invention include reconstructive surgery, removal of diseased osseous tissue and replacement with overlay or prosthesis, tightening of teeth, replacement of teeth, repair of traumatic injury, and the like. Precise means for applying the collagen preparations of the invention is dependent on the nature of the bone defect and the procedure selected to counteract it, as will be understood by those skilled in the art. However, in general, the compositions of the invention can be made into a paste or gel and molded into the defect by surgically packing the paste into the defect. The collagen preparation may also be injected into the defect when mixed so as to form a thinner suspension. In all cases, however, the defect to be treated must first be cleansed in such a way so as to expose fresh bone surface so that living bone cells are placed in communication with the defect. The fresh bone surface is required in order to provide a source of osteoprogenitor cells needed to synthesize the permanent bone structure.

B.2 Collagen Preparations

Native collagen consists in large part of a triple helical structure containing repeating triplet sequences composed of glycine linked to two additional amino acids, commonly proline and hydroxyproline; thus, glycine appears in every third position in the chain. In addition, all collagen chains contain regions at each end which do not have the triplet glycine sequence and are thus not helical. These regions are thought to be responsible for the immunogenicity associated with most collagen preparations. Immunogenicity can, in large part, be mitigated by removal of these regions to produce "atelopeptide" collagen. This can be accomplished by digestion with proteolytic enzymes such as trypsin, chymotrypsin, papain, or pepsin. Because of differing specificities of these proteases, the degree of completeness of removal of the telopeptides varies. Thus certain proteases, which effect the most complete removal, are preferred. Included among these is trypsin, which results in removal of substantially all of the telopeptide portions.

The non-helical telopeptide regions are also responsible for forming the cross-links which aid in stability of the fibrillar structure. These regions contain aldehydes capable of cross-linkage to lysine residues. Atelopeptide collagen must be cross-linked artificially, if it is so desired.

While all collagens share the foregoing characteristics, they have been subclassified into approximately ten types depending on the precise amino acid sequence in the individual chains of the triple helix, the carbohydrate content, and the presence or absence of disulfide cross-linking. The most common subtypes are Type I which is present in skin, tendon, and bone, and which is made by fibroblasts, and Type III which is found primarily in skin. Other types reside in specialized membranes or cartilage or at cell surfaces. Types I and III contain similar numbers of amino acids in their helices; however, Type III (but not Type I) contains two adjacent cysteines at the C-terminal ends of the triple helix which are capable of forming interchain cross-links.

Type I collagen contains one $\alpha 2(I)$ and two $\alpha 1(I)$ chains each of which contains 1014 amino acids in its triplet region; there are several carbohydrate moieties present on each chain. Type III collagen contains only $\alpha 1(III)$ (3 chains) which contain 1026 residues in their triplet regions. As stated above, the presence in Type III of a pair of adjacent cysteine residues at the carboxy terminal end of the triplet region results in stability of the interchain cross-links. Both collagens contain short non-triplet ends (telopeptides). The reconstituted fibrillar atelopeptide skin collagen used in this invention contains the atelopeptide forms of both Type I and Type III; the bone collagen powder consists of the atelopeptide form of Type I exclusively.

The Skin-Derived Collagen

The atelopeptide reconstituted fibrillar skin collagen preparations useful in the compositions of this invention are typified by the purified calfskin-derived atelopeptide collagen reconstituted fibrillar suspensions sold commonly under the trademark ZYDERM ® collagen implant (ZCI).

This and other preparations of skin-derived purified atelopeptide, reconstituted fibrillar collagen are well known in art. ZCI has been used extensively in soft tissue applications, including most prominently, the removal of wrinkles and depressed scars by injection of the preparation just under the skin. However, such preparations have not been used for bone repair except in conjunction with supporting materials which also contain OF and thus are directed to inductive bone repair. Such applications are disclosed in U.S. Ser. No. 348,414, filed Feb. 12, 1982.

As this collagen preparation is derived from calf skin, it contains mainly Type I collagen with approximately 1-5% Type III. The atelopeptide collagen is sterilized while still in solution by suitable filtration techniques and thus is not degraded or cross-linked. It is reconstituted into fibrillar form and packaged under sterile conditions. Detailed instructions for the preparation of atelopeptide reconstituted fibrillar skin collagen are found in U.S. Pat. No. 3,949,073 and U.S. Pat. No. 4,440,750, both incorporated herein by reference. A number of alternatives as to minor parameters are permissible, but the process must involve solubilization in acid solution, treatment with non-collagenase proteases to effect telopeptide removal, and reprecipitation under conditions which restore fibrillar structure.

The Lyophilized Skin Collagen

When the foregoing collagen material is lyophilized to form lyophilized collagen gel (LCG), it exhibits enhanced ability to entrench itself in the implanted or filled cavity and to resist mobilization from the desired location due to its superior structural integrity. In addition, LCG matrices continue to exhibit the desirable and necessary property of supporting the healing and regrowth of bone tissue into the implanted area. As described in further detail below, the LCG preparations of the invention may be prepared over a range of physical properties which are controlled by the pH, freezing rate, and concentration of the suspension during lyophilization. Whatever the properties desired, the LCG preparations of the invention are partially characterized in that they consist of atelopeptide reconstituted fibrillar skin collagen substantially free of impurities. If the preparation has been sterilized by microfiltration and processed under sterile conditions thereafter, it is also substantially free from cross-linking. The added lyophilization process results in a mat which is of sufficient cohesiveness to allow it to be easily cut simply using scissors or sharp blade, into the appropriate shape for clinical application. Wetting the mat produces a putty-like material which can be formed into any desired shape and placed into the defect.

Others have disclosed forms of lyophilized collagen for medical applications. These collagen preparations, however, differ from those of the present invention as do the applications. Battista, U.S. Pat. No. 3,471,598, discloses a lyophilized form of a preparation of an intermediate microcrystalline form of collagen, which is obtained by treatment of bovine skin with hydrochloric acid to swell and separate the collagen fibers. The collagen is not purified nor are the telopeptides removed. The material so prepared is regarded as being suitable for water absorbent sponges; clearly, the impure nature and the immunogenicity of such preparations would make them relatively undesirable for direct medical use. In addition, the acid used to prepare the intermediate form remains in the sponge. Kuntz, et al, U.S. Pat. No. 3,368,911, disclose an alternate method of preparing absorbent collagen sponges so as to be devoid of the acid, which substitutes carbonic acid for the comparatively non-volatile acids used in Battista. While the preparation is disclosed to employ substantially pure collagen fibrils, the telopeptides have not been removed. Miyata, U.S. Pat. No. 4,294,241, discloses lyophilized collagen sheets for skin dressing. These sheets are prepared from atelopeptide collagen reconstituted into fibrils; however, they differ from the LCG of the present invention in that they are artificially cross-linked. Ries, in U.S. Pat. No. 4,066,083, discloses the method of preparation of the commercially available product, Collagenfleece ®, for wound treatment. Luck and Daniels, U.S. Pat. No. 4,233,360, describe a lyophilized preparation which results in a foam rather than the mats of the present invention.

In general, the LCG of the present invention is prepared from a purified reconstituted fibrillar atelopeptide collagen such as, for example, Zyderm ® I collagen implant or Zyderm ® II collagen implant, both trademarks for atelopeptide reconstituted collagen preparations prepared from bovine skin. Other sources of the reconstituted purified skin collagen can be used, such as, for example, the skins of other mammals. In any event, however, the starting material must be prepared from these sources by processes which result in essentially pure collagen fibrils which are reconstituted from the solubilized form. In addition, the telopeptides must have been removed by suitable processes, such as, for example, trypsin digestion. Typically, such purified preparations are prepared by finely dividing the starting material, treating it with enzymes and/or suitable conditions of pH so as to destroy or extract non-collagen materials, treating the collagen with a digestive enzyme such as trypsin to remove the telopeptides, microfiltering to sterilize, and reconstituting the collagen fibrils by appropriate adjustment of pH and salt concentration, i.e., from acidic to neutral. Such preparations are known in the art, and indeed, the results thereof are commercially available.

The use of reconstituted collagen to prepare the lyophilized form is significant also from the perspective of non-degradative sterilization processes. As the collagen is, at one point in its preparation, in solubilized form, sterilization can be conducted by microfiltration—an entirely neutral process which causes no significant chemical or physical change in the structure. If further steps are then carried out under sterile conditions, so that no further sterilization is necessary, the resultant product is neither degraded or cross-linked as would be the case if more harsh sterilization methods, such as heat or γ-irradiation were used.

In preparing the LCG of the invention a suspension of suitable collagen is brought to a concentration of approximately 20–100 mg/ml and cast into molds or extruded into sheets. These forms are then frozen at about $-10°$ C. to $-50°$ C. and lyophilized at approximately 10–100 millitorr with a condenser temperature at about $-45°$ C. to $-55°$ C., and the shelf temperature at approximately $-30°$ C. Lyophilization is carried out for 1–7 days before increasing the shelf temperature to approximately 15° C.–25° C. for about 24 hours before removing the LCG from the lyophilizer.

Alternatively, a solubilized form of an atelopeptide purified collagen can be used directly. Such a solution is obtained by dissolving purified atelopeptide collagen in aqueous solution at about pH 2–3, optionally sterilizing by microfiltration, and precipitating the reconstituted form by bringing the pH to approximately neutrality with, for example, phosphate buffer. The resulting precipitated collagen is harvested by centrifugation, and a pelleted collagen resuspended in neutral buffer and treated as set forth above.

An alternative method of lyophilization which yields, for some applications, superior results, is a modified form of the foregoing procedure. The collagen suspension is cast into sterile culture plates (e.g., 35 mm), and the resulting cast is smoothed, e.g., with a spatula. The casts are then frozen and held at approximately $-100°$ C. to $-50°$ C., preferably around $-80°$ C. for about one hour prior to lyophilization. Lyophilization is conducted at about 10–100 millitorr over approximately 24 hours until dry to yield porous mats a few mm thick.

Bone-Derived Collagen

The bone collagen powder (BCP) used herein is derived from demineralized bone, and its collagen component is, accordingly, Type I collagen exclusively. This collagen preparation is a new material not identical in physical or chemical characteristics to previously prepared forms of collagen and is conveniently stored as a dried powder. In general, bone, for example, bovine, porcine, or other mammalian bone, preferably compact bone, is cleaned, frozen, pulverized and demineralized in hydrochloric acid, or other suitable acid, using standard techniques. The residual organic matter is then separated and digested using proteolytic enzymes sequentially or in combination. Neutral proteases, e.g., trypsin, which allow for the selective degradation of non-collagenous proteins are preferred, as described by Oliver and Grant in British applicatiom GB 1565340A. Certain acid proteases such as pepsin cause partial digestion of the collagen, and are not preferred. Non-proteinaceous bone components may also be removed using suitable enzymes such as chondroitinase, hyaluronidase, and various nucleases if digestion is necessary to remove them. Of course, the use of collagenase is inappropriate. After treatment with the appropriate enzymes, the digestion products are removed by salt extraction and lipids by extraction in moderately polar solvents such as acetone, chloroform, or ether. The insoluble extracted material consists of purified atelopeptide collagen in the form of BCP. It may be used after sterilization by known methods such as gamma irradiation or heat. The cross-linking of this type of collagen is often desirable since any residual antigenic effects of any telopeptide portions remaining after trypsin treatment are thus mitigated.

The resulting BCP is novel. It consists essentially of Type I collagen which apparently retains the original molecular architecture of the bone collagen and is free of the telopeptides.

The BCP is resuspended in physiological buffer for use in compacting into a properly prepared bone defect.

Mixtures

If mixtures are used to form the implants or paste repair material of the invention, these are obtained using suspensions of reconstituted fibrillar atelopeptide collagen, such as ZCI, and BCP in a range of proportions depending on the physical properties needed to handle the material and to cope with the degree of stress expected to be imparted to the repaired region. Increased amounts of BCP permit additional weight-bearing and stress-tolerating properties to be built into the composition, whereas decreasing its proportion relative to ZCI results in greater flexibility and ease of application. Thus, the method of the invention offers greater versatility in adapting the nature of the repair to the subject defect than do the methods known in the art.

The range of applications is of course large as either component can be used alone. As the preferred mixture is dependent on the nature of the defect, a general, single preferred range cannot be chosen. However, in general, for weight-bearing defects, a preferred range is from about 50% ZCI/50% BCP (by weight) to about 10% ZCI/90% BCP (by weight); for peridontal or superficial defects, a preferred range is from bout 90% ZCI/10% BCP to 50% ZCI/50% BCP (by weight). (All of the above ratios assume a 35 mg/ml suspension of ZCI, and the weights referred to are weights of the entire suspension.)

C. EXAMPLES

The following will illustrate but not limit the invention.

C.1 Preparation of ZCI

Zyderm ® collagen implant (available from Collagen Corporation, Palo Alto, CA) was used as the reconstituted fibrillar atelopeptide skin collagen preparation. The reconstituted native type collagen fibrils were provided at a concentration of about 35 mg/ml. The preparation had been sterilized during processing by filtration and thus was not subjected to degradative procedures such as heat or irradiation.

C.2 Preparation of LCG

A. Pepsin-solubilized bovine hide collagen in aqueous solution at about pH 2–3 which was sterilized by microfiltration was adjusted to pH 7.4 with phosphate buffer. The precipitated collagen was harvested by centrifugation and then suspended in phosphate buffer pH 7.4 to 35 mg/ml, thus generating a reconstituted fibrillar atelopeptide skin collagen. The suspension was cast into sheet form, and the sheets were frozen at −25° C. and then lyophilized at 25 millitorr with the condenser temperature at −50° C. The lyophilized sheets were then stored at −30° C. for 5 days before the temperature was again raised to 20° C. for 24 hr immediately prior to use.

B. In an alternative (and preferred) method, approximately 5 cc portions of ZYDERM ® Collagen Implant were cast into sterile 35 mm tissue culture plates and smoothed with a spatula. The collagen gel was frozen and held at −80° C. for approximately one hour. The frozen collagen gel was then lyophilized for approximately 24 hours until dry, to yield porous white disks 35 mm in diameter and 3 to 5 mm thick.

C.3 Preparation of BCP (Bovine)

Bovine femurs were manually cleaned of adherent soft tissue, and the articular ends of the bone removed near the epiphyseal plate to yield primarily compact bone. The bone shafts were cooled with liquid nitrogen ($LN_2$), split axially and the marrow removed. The compact bone pieces were crushed using a jaw crusher at $LN_2$ temperatures into chips 5 mm or less in size. The bone chips were pulverized in a hammermill, again under $LN_2$.

The bone powder was sieved under a stream of running water into two particle size fractions 125 to 250 $\mu$m and 250–425 $\mu$m. The two particle sizes were processed in parallel but separate paths.

The bone powder was demineralized in 0.5M HCl (25:1/vol:weight of bone powder) for three hours at room temperature with the acid replaced with fresh acid after 1½ hours. At the end of the demineralization step, the powder was washed three times with water to remove acid soluble materials. The demineralized bone powder was lyophilized preparatory to protease treatment.

The bone powder was digested with trypsin (bone powder 50 mg/ml, trypsin 2 mg/ml in 0.1M $Na_2HPO_4$ with 0.5 mg/ml $NaN_3$, pH 7.8; i.e., trypsin:bone powder=1:25). The enzyme digestion was carried on at 15° C. over a 10-day period. The digestion supernatant was assayed for soluble protein by the biuret method to monitor the course of digestion.

To remove trypsin digestion products, the bone powder was allowed to settle, the supernate was decanted, and 4M NaCl (10:1/vol:weight) was added to the solid. The bone powder was stirred at room temperature for 1 hr at which time the powder was allowed to settle and the supernatant was decanted. The 4M NaCl extraction was repeated for a total of three times.

To remove the sodium chloride, the bone powder was washed six times in 10 volumes of water USP water for injection (WFI) with 10 min stirring in an identical manner as described for the NaCl extraction.

The bone powder was then extracted two times with 10 volumes of acetone to remove any lipids present. Following the acetone extraction, the bone powder was washed five times with 10 volumes at WFI, vacuum filtered and lyophilized to yield bone collagen powder (BCP).

The BCP samples were analyzed chemically for lipid, glycosaminoglycan and amino acid composition, immunologically for residual trypsin, bovine red blood cells, and bovine collagen telopeptides (the antigenic terminal ends of collagen), and by electron microscopy for ultrastructure. With increasing trypsin treatment, preferably 4 to 10 days, the BCP became an increasingly pure bovine Type 1 collagen with the telopeptides largely unavailable. There was no residual trypsin. Electron microscopy showed collagen fibrils with the characteristic band pattern and organization of bovine bone. The amino acid composition showed chemically pure collagen.

The BCP's so prepared were of the two particle sizes and varying degrees of trypsin treatment as summarized in Table 1. All samples were sterilized with $\gamma$-irradiation at 1.5 Mrad.

TABLE 1

Summary of BCP Samples

| ID Numbers | Particle Size ($\mu$m) | Days of Trypsinization |
|---|---|---|
| 2Z | 125–250 | 0 |
| 2A | 125–250 | 1 |
| 2B | 125–250 | 4 |
| 2C | 125–250 | 10 |
| 3Z | 250–425 | 0 |
| 3A | 250–425 | 1 |
| 3B | 250–425 | 4 |
| 3C | 250–425 | 10 |

C.4 Preparation of BCP and ZCI Mixture

The bone collagen powders (BCP), designated 2C and 3C in the paragraph above, were mixed in a 55/45% by weight ratio, and the mixture was sterilized by 1.5 mrad $\gamma$-irradiation.

Two batches of BCP/ZCI mixtures were prepared using this sterilized BCP mixture: A mixture of 33% BCP in ZCI was prepared by mixing 0.33 g BCP (dry) with 0.67 g of ZCI (as a 35 mg/ml suspension—i.e., approximately 0.67 g×0.035 g/ml of solid). A second mixture was prepared by mixing 0.17 g BCP with 0.83 g of ZCI (35 mg/ml suspension). Each of these materials was mixed thoroughly and filled into 1¼ cc syringes for use in the procedures below.

C.5 Repair of Bone Defect with ZCI

Forty-five rats between 6 and 8 weeks old were anesthetized, the scalp reflected and the cranial periosteum removed. Bilateral 3×7 mm full thickness defects were placed in the parietal bones of the cranium with a dental burr. The injectable collagen gel as described in C.1 was packed into the defects with the aid of a small spatula and the scalp replaced and sutured. The rate of healing within the defects was monitored by X-ray and histology at 2, 4, 8, and 16 weeks post-implantation.

After 2 weeks, islands of new bone cells (osteoblasts) and matrix could be observed histologically within the collagen gel. By 4 weeks, new bone spanned the entire defect in a majority of the cases and fusion between the cut edges of the defect and this new bone was beginning to occur. Between 8 and 16 weeks the union between old and new bone became barely perceptable. Also, new bone was remodeled into layers of compact bone with well-defined marrow cavities typical of pre-existing bone at the site of the defect. X-ray of the skulls after removal from the animals confirmed the presence of extensive radio-opaque bone in the defects at 16 weeks. Animals with non-implanted bilateral parietal defects failed to show significant healing during the 16-week observation period. In the latter cases, osteogenic activity was limited to a small area at the cut edges of the defects with the remainder of the defect being filled with loose connective tissue.

Thus reconstituted collagen fibers provide a novel and useful method of obtaining a matrix support for conductive bone growth.

C.6 Repair of Cranial Defects Using LCG

Rats approximately 8 weeks old were anesthesized, the scalp reflected and the cranial periosteum removed. Bilateral 3×7 mm full thickness defects were placed in the parietal bones of the cranium with a dental burr. The lyophilized collagen as prepared in C.2.B was cut into strips slightly larger than the defects so as to effect a tight seal between the defect and the implant. Some of the strips were placed in the defects dry and allowed to hydrate in situ while others were prehydrated prior to implantation. After implantation, the scalp was repositioned and sutured. The rate of healing within the defects was evaluated by histology at 2 and 4 weeks post-implantation.

At 2 weeks, the implants were well infiltrated with connective tissue cells and blood vessels but new bone formation was very limited. While non-implanted defects of the type described in the previous paragraph did not heal and remained filled with soft tissue, the repaired defect showed areas of new bone forming throughout the implant by 28 days. Early evidence of fusion with pre-existing bone could be seen at the interface of the cut edges of the defect and the implant. By 56 days mature bone with well-defined marrow cavities were present throughout the defect.

LCG is easily cut and manipulated to form inserts capable of supporting conductive bone growth. The lyophilized reconstituted collagen fiber mats which are obtained provide a convenient and suitable material for this purpose.

C.7 Use of BCP in Bone Repair

Rats, 6 week old, were anesthetized and 3×7 mm defects were created in the left and right parietal bones of the skull. Bone was removed to full thickness of the skull with a dental burr, and the BCP, as prepared above, and wet with sterile saline was packed into the defect. Control defects were left unfilled. BCP samples 2B, 3Z, 3A, 3B and 3C (Table 1) above were tested. Samples were taken and histology done at 2 and 4 weeks after implantation.

Samples 3Z (no trypsin digestion) and 3A (1 day trypsin) showed inflammation with evidence of an antigenic component. Samples 2B, 3B and 3C at 2 weeks showed a multinucleate cell response, digestion of the BCP with a concomitant osteoblast response, and the deposition of new compact bone. At 4 weeks bone formation was extensive throughout the implant with evidence of fusion of new and old bone. Control defects showed only slight bone growth at the cut edges.

The sera of rats receiving BCP sample 3Z contained circulating antibodies to the BCP. The other BCP samples tested did not elicit an antibody response.

These results are summarized in Table 2.

TABLE 2

| | Histology and Serology in the Rat Parietal Model at 28 Days | | | |
|---|---|---|---|---|
| BCP Sample | Bone Formation | Multinucleate Cells | Macrophages & Lymphocytes | Circulating Antibodies |
| 3Z | + | ++ | + | + |
| 3A | + | + | + | − |
| 3B | ++ | + | − | − |
| 3C | ++ | + | − | − |
| 2B | ++ | + | − | − |

C.8 Peritoneal Lavage Assay for Immunogenic Response of BCP

BCP samples 2Z, 2A, 2B and 3B, 30 mg suspended in 7 ml phosphate buffered saline (PBS), were injected intraperitoneally into rats. At 1, 3, 14 and 27 days the peritoneum was lavaged with 100 ml PBS and a differential and total cell count was performed as a quantitative measure of inflammation. The BCP implant was examined histologically and sera were taken for measurement of circulating antibodies.

All samples showed a transient neutrophil response at 1 day, probaly related to the particulate nature of the material. At 3, 14 and 28 days, the responding cells were predominantly macrophages with extensive digestion of the BCP evident at 28 days by histology of the implant. Very few immunocompetent cells (lymphocytes) were present at any time. Serology showed rats receiving 2Z developed significant antibody titers against the BCP. Rats receiving 2A, 2B, 2C, or 3B did not develop an antibody response.

BCP provides a novel matrix material derived from bone useful in effecting bone repair by a conductive mechanism. A suspension of the bone collagen powder (BCP) can be shaped into bone defects and provides a stress-bearing replacement for lost bone and which supports new bone growth.

C.9 Use of the BCP/ZCI Mixture in Bone Repair

Twenty-four rats, 6 and 8 weeks old, were anesthetized, and 3×7 mm defects were created in the left and right parietal bones of the skull. Bone was removed to full thickness of the skull with a dental burr, and the two lots of the BCP/ZCI mixtures, as prepared above, were packed into the defects. Control defects were filled with BCP alone, ZCI alone, or left unfilled. Samples were taken and histology done at 2 and 4 weeks after implantation.

Early bone formation occurred in the defects filled with BCP/ZCI mixtures at 2 weeks post-implantation. However, the mixtures were not always uniform so that the pattern of bone formation varied depending on the predominant type of collagenous implant present (i.e., BCP or ZCI) in a given region of the defect.

By 4 weeks bone formation was extensive in the ZCI component of the mixture and BCP particles were being incorporated into centers of new osteogenic activity. This, coupled with early remodeling, gave the new bone spanning the defects a more uniform appearance than that seen at 14 days. Both implanted control defects (i.e., BCP alone and ZCI alone) showed osteogenic activity characteristic of the patterns observed in previous studies. Non-implanted controls showed only slight bone growth at the cut edges of the defects.

By varying the relative amounts of purified atelopeptide reconstituted fibrillar collagen, which forms a resilient, gel-like suspension, and of bone collagen powder, which offers compressive strength, implants are formed which offer versatility and effectiveness in providing an appropriate matrix for bone repair by conduction.

We claim:

1. A method of effecting conductive repair of a bone defect in a mammal, which method comprises:
    (a) exposing fresh bone surface comprising living osteoprogenitor cells to the defect;
    (b) placing into the defect and into contact with the fresh bone surface a preparation of collagen selected from the group consisting of:

(1) a composition consisting essentially of Type I collagen derived from demineralized, protease-treated, delipidized bone;
(2) a lyophilized gel of purified atelopeptide reconstituted fibrillar skin collagen; and
(3) mixtures of (1) and purified atelopeptide reconstituted fibrillar skin collagen.

2. The method of claim 1 wherein the preparation of collagen in (2) is prepared from calf skin.

3. The method of claim 1 wherein the preparation of collagen in (2) is in the form of a mat or sheet.

4. The method of claim 1 wherein the preparation of collagen in (2) is substantially free of cross-linking.

5. A purified collagen preparation consisting essentially of Type I collagen derived from demineralized, protease-treated, delipidized bone.

6. A process for preparing bone collagen powder, which bone collagen powder is a composition consisting essentially of Type I collagen derived from demineralized, protease-treated, delipidized bone, which process comprises:
(a) treating demineralized bone powder with at least one protease selected from trypsin and pepsin to obtain soluble products and a collagen-containing residue;
(b) extracting the soluble products,
(c) recovering the residue, and
(d) extracting the residue with a solvent to obtain a delipidized form of the residue as bone collagen powder.

7. Bone collagen powder prepared by the process of claim 6.

8. The process of claim 6 which further includes enzymatically treating the demineralized bone to remove non-proteinaceous bone components.

9. The method of claim 6 wherein the solvent is selected from acetone, chloroform, and ether.

10. The method of claim 6 which includes the further step of sterilization of the bone collagen powder.

* * * * *